United States Patent
Piccardi et al.

(10) Patent No.: US 9,901,535 B2
(45) Date of Patent: Feb. 27, 2018

(54) USE OF A COMBINATION OF TAURINE OR A DERIVATE THEREOF AND A GRAPE EXTRACT FOR IMPROVING THE QUALITY OF THE NAILS

(71) Applicant: NUTRICOS TECHNOLOGIES, Clichy (FR)

(72) Inventors: Nathalie Piccardi, Arceau (FR); Yann Mahe, Sainte Genevieve des Bois (FR); Carole Bru, Courbevoie (FR)

(73) Assignee: NUTRICOS TECHNOLOGIES, Clichy (FR)

( * ) Notice: Subject to any disclaimer, the term of this patent is extended or adjusted under 35 U.S.C. 154(b) by 0 days.

(21) Appl. No.: 14/432,438

(22) PCT Filed: Sep. 27, 2013

(86) PCT No.: PCT/IB2013/058932
§ 371 (c)(1),
(2) Date: Mar. 30, 2015

(87) PCT Pub. No.: WO2014/049563
PCT Pub. Date: Apr. 3, 2014

(65) Prior Publication Data
US 2015/0250708 A1    Sep. 10, 2015

(30) Foreign Application Priority Data

Sep. 28, 2012   (FR) ..................... 12 59223

(51) Int. Cl.
| | |
|---|---|
| *A61K 8/97* | (2017.01) |
| *A61K 8/27* | (2006.01) |
| *A61K 8/46* | (2006.01) |
| *A61Q 3/00* | (2006.01) |
| *A61K 8/67* | (2006.01) |
| *A23L 33/105* | (2016.01) |
| *A23L 33/15* | (2016.01) |
| *A23L 33/16* | (2016.01) |
| *A23L 33/175* | (2016.01) |

(52) U.S. Cl.
CPC .............. *A61K 8/97* (2013.01); *A23L 33/105* (2016.08); *A23L 33/15* (2016.08); *A23L 33/16* (2016.08); *A23L 33/175* (2016.08); *A61K 8/27* (2013.01); *A61K 8/466* (2013.01); *A61K 8/673* (2013.01); *A61K 8/676* (2013.01); *A61Q 3/00* (2013.01); *A23V 2002/00* (2013.01); *A61K 2800/88* (2013.01); *A61K 2800/884* (2013.01); *A61K 2800/92* (2013.01)

(58) Field of Classification Search
None
See application file for complete search history.

(56) References Cited

U.S. PATENT DOCUMENTS

| | | | | |
|---|---|---|---|---|
| 4,132,777 | A * | 1/1979 | van Os ................ | A61K 9/0017 424/119 |
| 5,013,545 | A * | 5/1991 | Blackman ............ | A61K 9/0014 424/443 |
| 2005/0175565 | A1* | 8/2005 | Duranton ............. | A23L 1/3002 424/70.1 |
| 2006/0269508 | A1 | 11/2006 | Trejo | |
| 2010/0086521 | A1 | 4/2010 | Trejo | |
| 2011/0104135 | A1 | 5/2011 | Trejo | |
| 2011/0106730 | A1 | 5/2011 | Trejo | |

FOREIGN PATENT DOCUMENTS

WO    2006/104730 A1    10/2006

OTHER PUBLICATIONS

"Night Multivitamin for Women," Nature's Way Rest & Restore, Sep. 2011, XP002700119.
"Phyto Citrus Masque Restructurant 200ML," May 14, 2012 Retrieved from the Internet: URL:http://wayback.archive.org/web/20120514195411/http://www.parapharma3000.com/cheveux/2573-phyto-citrus-masque-restructurant-200ml-7573319.html.
"Beauté et Santé des Cheveux et des Ongles," Nutra News: Science, Nutrition, Prévention et Santé, Jun. 2008 Retrieved from the Internet:    URL:http://www.nutranews.org/data/pdf/numeros/fr/nutranews200806.pdf.
Colombo Victor E., PhD et al. "Treatment of Brittle Fingernails and Onychoschizia with Biotin: Scanning Electron Microscopy," Journal of the American Academy of Dermatology, vol. 23, No. 6, Dec. 1, 1990, pp. 1127-1132.
Jun. 20, 2014 International Search Report issued in International Patent Application No. PCT/IB2013/058932.
Jun. 20, 2014, International Written Opinion issued in International Patent Application No. PCT/IB2013/058932.
Jul. 5, 2013 French Written Opinion issued in Patent Application No. FR 1259223.
"Inneov Masse Capillaire Cheveux Colorés-Boite 2×60 Comprimés," May 14, 2012 Retrieved from the Internet: URL:http://wayback.archive.org/web/20120514195411/http://www.parapharma3000.com/cheveux/2597-inneov-fermete-duo-boite-2x40-caps-2601789.html.

* cited by examiner

*Primary Examiner* — Jennifer A Berrios
(74) *Attorney, Agent, or Firm* — Oliff PLC

(57) ABSTRACT

The invention relates to the oral cosmetic use of a combination of active agents comprising at least taurine, a derivative thereof and/or an acceptable salt thereof and at least one grape extract, as cosmetic active agents for improving the quality of the nails. More particularly, the present invention relates to the oral cosmetic use of such a combination for improving the solidity of the nails and for reducing and/or preventing their splitting.

17 Claims, No Drawings

USE OF A COMBINATION OF TAURINE OR A DERIVATE THEREOF AND A GRAPE EXTRACT FOR IMPROVING THE QUALITY OF THE NAILS

The present invention relates to the field of cosmetic products and food supplements for improving the quality of the nails.

More particularly, the present invention proposes the use of a novel combination of active agents for reducing and/or preventing aesthetic defects, and/or for improving the solidity or hardness of the nails. The invention is also directed towards the use of a combination of active agents in accordance with the invention for reducing and/or preventing splitting of the nails.

The present invention also relates to a cosmetic process for reducing and/or preventing brittle, fragile, soft, split or cracked nails, preferably split nails, in an individual in need thereof, characterized in that it comprises at least the oral administration, to the said individual, of a combination or of a composition in accordance with the invention.

A nail or ungual plaque is a flexible, sleek and translucent horny blade which forms a surface excrescence of the skin, consisting of keratinocytes and a very dense and homogeneous keratin matrix. This matrix keeps the cells welded together and gives the nail its strength, hardness, solidity and flexibility. The nail is enveloped by an epidermal sheath, or matrix.

From a morphological viewpoint, a nail consists of a dorsal part, an intermediate part, a ventral part, a proximal matrix, an intermediate matrix, a lunula and the nail bed. 80% of the thickness of a nail is produced by the proximal matrix, and 20% of its thickness is produced by the intermediate matrix and the nail bed. The dorsal part consists of hard keratin, the intermediate part is the thickest and is formed of moderately hard keratin, and the ventral part consists of soft keratin.

As regards its chemical constitution, a nail contains water, lipids, mucopolysaccharides and minerals, such as sodium, potassium, iron, calcium, zinc or silicon.

The hardness and flexibility of nails depend especially on the orientation of the keratin fibres, the arrangement of the keratinocytes and their cohesion and chemical constitution, in particular the content of water, lipids and phospholipids.

Many factors may impair the chemical constitution of the nails, and as a result their hardness or shape.

Among the extrinsic factors that are liable to affect the nails, mention may be made of exposure to sunlight, exposure to temperature and/or humidity variations, and exposure to pollutants or to cigarette smoke. Among the intrinsic factors affecting the nails, mention may be made of stress, fatigue, hormonal changes, dehydration, a metabolic deficit, ageing or certain pathologies.

These various factors are prone to make the nails fragile or brittle, affect their shape, make them split, and thus greatly reduce their aesthetic appeal.

At the present time, the main solutions proposed in the field of nail quality are based on the use of nail varnishes, of moisturizing active agents in handcare products, or of chemical reinforcement of the nail. The latter solution is based on the use of nail-hardening agents, such as formaldehyde at 1-2%, which generate crossbonds in the keratin. However, frequent use of these products may give rise to too many crossbonds, paradoxically promoting embrittlement of the nails.

Temporary implants, such as false nails, have also been proposed in the field of nail quality, but the main aim thereof is to hide the poor quality of the nails rather than to prevent and/or restore their quality.

From a cosmetic viewpoint, there is thus a need to be able to reduce or prevent the various aesthetic impairments that may affect the nails, irrespective of the origin of these impairments.

There is also a need for novel active agents or for a combination of active agents that can exert efficient and beneficial action on the quality of the nails, and in particular on their hardness, their solidity, their resistance to impacts or to external attacking factors, their resistance to splitting, their smooth appearance, their sheen and consequently their general aesthetic appearance.

There is more particularly a need for novel active agents or a combination of active agents that are capable of exerting efficient action on the solidity of the nails and of reducing and/or preventing their splitting.

The object of the present invention is to satisfy these needs.

Thus, according to a first aspect, the present invention relates to the oral cosmetic use of a combination of active agents comprising at least taurine, a derivative thereof and/or an acceptable salt thereof and at least one grape extract, as cosmetic active agents for improving the quality of the nails.

Taurine has already been described in the prior art, either as a cell activator for regulating hair cells, proposed as a hair stimulator for topical application (WO 02/24189), or as an agent that is useful for improving hair density, via oral administration (WO 2004/000 293).

To the inventors' knowledge, it has never been proposed or suggested hitherto that the oral administration, to an individual in need thereof, of a combination of taurine, a derivative thereof and/or an acceptable salt thereof, and of at least one grape extract, as active agents, could prove to be particularly effective for improving the quality of the nails.

More particularly, the oral administration of a cosmetic combination in accordance with the invention makes it possible to make the nails more solid, and thus to reduce and/or prevent the nails from breaking and/or splitting.

More particularly, the oral administration of a cosmetic combination in accordance with the invention makes it possible to reduce and/or prevent lamellar and/or transverse separations of the nails, and especially their splitting.

More particularly, the oral administration of a cosmetic combination in accordance with the invention makes it possible to improve the hardness of the nails, and thus to reduce and/or prevent soft or overly flexible nails.

More particularly, the oral administration of a cosmetic combination in accordance with the invention makes it possible to improve the general aesthetic appearance of the nails, and especially to reduce and/or prevent striated and/or damaged nails.

More particularly, the oral administration of a combination in accordance with the invention makes it possible to improve the sheen and/or transparency of the nails.

Furthermore, due to the improvement in the quality of the nails associated with the oral administration of a cosmetic combination in accordance with the invention, such an administration also advantageously makes it possible to have longer nails. This also makes it possible to facilitate the staying power of nail varnishes.

More particularly, the oral administration of a cosmetic combination of active agents in accordance with the invention makes it possible to improve the aesthetic appearance of the cuticle of the nails.

The administration of a combination in accordance with the invention also enables the nails more quickly to regain a sleek and shiny appearance after the removal of false nails and/or to be protected in the event of the application of false nails.

Thus, and as demonstrated in the examples, an administration for 3 months of a combination in accordance with the invention makes it possible to reinforce the quality of the nails. In particular, it enables the nails to become harder, less brittle, more resistant to impacts, less prone to splitting and to have a sleek, homogeneous and translucent appearance, and also an improved general aesthetic appearance, especially with less damaged and less striated, or even unstriated, nails.

According to a preferred embodiment, the combination in accordance with the invention also comprises, as additional active agent, zinc or a salt thereof, and preferably zinc gluconate.

According to a more preferred embodiment, the combination in accordance with the invention also comprises, as additional active agents, vitamins, especially vitamin B8 and/or vitamin C, preferentially vitamin B8 and vitamin C.

According to one embodiment, the combination in accordance with the invention may be used in a cosmetic composition that is suitable for oral administration.

A cosmetic composition in accordance with the invention gives the same advantages as those afforded by the combination in accordance with the invention, as indicated previously.

According to yet another of its aspects, the subject of the present invention is a cosmetic treatment process for improving the quality of the nails, in an individual in need thereof, characterized in that it comprises at least the oral administration, to the said individual, of a combination or of a composition in accordance with the invention.

The use of a combination of active agents in accordance with the invention is necessarily performed in an effective amount, i.e. an amount that enables the active agents to manifest their properties with regard to the improvement to be afforded to the quality of the nails.

For the purposes of the present invention, the term "prevent" means reducing to a lesser extent the risk or probability of manifestation of a given phenomenon, i.e. in the present invention impairment of the quality or aesthetic appearance of the nails.

The present invention describes a combination of active agents comprising, or even consisting of, at least taurine, a derivative thereof and/or an acceptable salt thereof, at least one extract of grape seeds, zinc or a salt thereof, and vitamin B8. Preferably, a combination according to the invention also comprises vitamin C.

According to yet another of its aspects, the present invention relates to a cosmetic composition that is suitable for oral administration, comprising at least taurine, a derivative thereof and/or an acceptable salt thereof, at least one extract of grape seeds, zinc or a salt thereof, and vitamin B8, wherein taurine, a derivative thereof and/or an acceptable salt thereof is used in a content of between 1% and 30% by weight relative to the total weight of the composition, expressed as taurine equivalent. Preferably, a cosmetic composition according to the invention also comprises vitamin C.

For the purposes of the present invention, the term "splitting of the nail" means both lamellar splitting (or onychoschizia) and longitudinal separation of the nail (or onychorrhexis). Preferably, for the purposes of the present invention, the term "splitting of the nail" means lamellar splitting (or onychoschizia).

The term "onychoschizia" means the deterioration of the intracellular adhesion factors of the nails, which is characterized by lamellar cracking of the end of the nail and also of its distal portion. [Van de Kerkhof et al., 2005; Kechijian, 1985].

The term "onychorrhexis" means a state characterized by vertical cracking or ridges on the nails.

According to yet another of its aspects, the present invention relates to a packaging kit or assembly comprising:
  (i) a combination in accordance with the invention intended for oral administration, and
  (ii) an antifungal agent intended for topical application,
  the combination (i) and the antifungal agent (ii) being intended to be administered independently of each other, separately, simultaneously or consecutively over time, the antifungal agent (ii) advantageously being administered before the combination (i).

According to yet another of its aspects, the present invention relates to a packaging kit or assembly comprising:
  (i) a combination in accordance with the invention intended for oral administration, and
  (ii) a moisturizer and/or a hardener intended for topical application,
  the combination (i) and the moisturizer and/or hardener (ii) being intended to be administered independently of each other, separately, simultaneously or consecutively over time.

The present invention also describes a packaging kit or assembly comprising:
  (i) a combination of active agents in accordance with the invention intended for oral administration, and
  (ii) a nail varnish intended for topical application to at least one nail.

The present invention also describes a packaging kit or assembly comprising:
  (i) a combination of active agents in accordance with the invention intended for oral administration, and
  (ii) at least one false nail intended to be applied topically onto at least one nail.

Taurine, Derivatives Thereof and Acceptable Salts Thereof

As active agents that are present in a combination in accordance with the invention, use is made of taurine and/or a derivative thereof and/or an acceptable salt thereof.

Taurine, or 2-aminoethanesulfonic acid, is an amino acid derivative. It is naturally present ubiquitously in the human body.

It is involved, for example, in the mechanism of fat digestion since it is present in the structure of bile acids (taurocholic and taurochenodeoxycholic acids), precursors of emulsifier-charged bile salts (in the form of micelles) of food lipids (especially including cholesterol) arriving in the duodenum after a meal.

However, the physiological/physiopathological action and the role of taurine remains disputable (Huxtable et al., 1992, *Physiol. Research,* 72: 101-103; Hansen et al. 2001, Metab. Res. Rev., 2001, 17: 330-346).

For the purposes of the present invention, the term "taurine derivatives" means structural analogues of taurine, metabolites thereof or acceptable salts thereof.

Such structural analogues are, for example, 4-(2-hydroxyethyl)-1-piperazineethanesulfonic acid, N-acyltaurine, acetylhomotaurine, N,N-diacetylsalicyloxyethyltaurine, acylmethyltaurine, homotaurine or salts thereof as described in *Taurine analogues; a new class of therapeutics: retrospect and prospects*, Gupta et al., S. Curr. Med. Chem. 2005; 12(17): 2021-39.

A taurine metabolite is, for example, hypotaurine.

The term "acceptable salts" means salts chosen for their total harmlessness, insofar as the compositions in accordance with the invention are intended to be administered to an individual. In this respect, alkali metal or alkaline-earth metal salts, in particular the magnesium, manganese, iron(II) or zinc salts, are most particularly suitable for use in the invention.

Taurine derivatives may also be natural extracts that are rich in taurine (2-aminoethanesulfonic acid) or derivatives thereof.

According to the invention, taurine or an acceptable salt thereof will preferably be used.

According to a preferred embodiment, taurine and/or hypotaurine will be used.

The taurine in accordance with the invention may be, for example, the product sold by the company Quimdis.

According to the invention, taurine, a derivative thereof and/or an acceptable salt thereof are used at daily doses ranging from 1 to 3000 mg per day, advantageously from 5 to 2000 mg per day and preferably from 10 to 300 mg per day.

According to a preferred embodiment, the daily dose is from about 50 to 150 mg per day.

The indicated doses of taurine derivatives or of a salt thereof in the present description are doses of taurine equivalent.

Grape Extract

A grape extract is naturally rich in polyphenols.

Polyphenols from the grape extracts in accordance with the invention may be in the form of monomers and/or oligomers. The polyphenols more particularly present in the grape extracts, especially in grape seed extracts, are polyphenols of the stilbenoid or tannin family, more particularly condensed tannins They are more particularly oligo-proanthocyanidin (OPC) polyphenols.

A grape extract in accordance with the invention preferably consists of a grape seed extract.

It may be, for example, the product sold under the name Vitoflavan 50 by the company DRT.

A grape extract in accordance with the invention is used so as to afford daily doses of polyphenols ranging from 0.1 to 2000 mg per day, advantageously from 10 to 1000 mg per day and preferably from 50 to 500 mg per day.

According to a preferred embodiment, the daily dose is from about 50 to 300 mg per day.

Thus, a combination of active agents in accordance with the invention advantageously comprises taurine or hypotaurine and a grape seed extract.

In the context of the present invention, the doses of grape extract represent the doses of polyphenols.

According to the present invention, taurine, a derivative thereof and/or an acceptable salt thereof and a grape extract in accordance with the invention are used in a ratio of taurine, a derivative thereof and/or an acceptable salt thereof/grape extract as described previously of between 1/5 and 5/1, preferably between 1/4 and 4/1 and even more preferably between 1/3 and 3/1.

Additional Active Agent(s)

A combination in accordance with the invention may also comprise one or more additional cosmetic active agents.

Advantageously, such an additional cosmetic active agent may be intended to reinforce the desired cosmetic effect as described previously.

As additional active agents that may be used, mention may be made of:

vitamins, such as vitamin A, $B_5$, $B_6$, $B_8$ or PP (vitamin $B_3$ or niacin), antioxidants, such as curcuminoids; carotenoids, especially a carotenoid chosen from β-carotene, astaxanthin, zeaxanthin and lutein or compounds containing the same, such as wolfberry or lactowolfberry; polyphenol compounds, flavonoids such as catechins; proanthocyanidins, anthocyanins, PCOs (procyanidol oligomers); ubiquinones; coffee extracts containing polyphenols and/or diterpenes; chicory extracts; Ginkgo biloba extracts; grape extracts rich in proanthocyanidins; pimento extracts; soybean extracts; cocoa or coconut milk; pomegranate; Emblica, minerals, such as zinc, calcium, magnesium, copper, iron, iodine, manganese, selenium and chromium(III), sugars, amino acids, especially sulfur amino acids such as glutathione precursors, selenium amino acids and citrulline, prebiotics, chosen especially from oligosaccharides, produced from glucose, galactose, xylose, maltose, sucrose, lactose, starch, xylan, hemicellulose, inulin, gums of acacia type, for example, or a mixture thereof. More particularly, the oligosaccharide comprises at least one fructo-oligosaccharide. More particularly, this prebiotic may comprise a mixture of fructo-oligosaccharide and of inulin, phytosterols, such as resveratrol, hesperidin and neohesperidin, orthosilicic acid and monomethylsilanetriol, arterial pressure modulators, and mixtures thereof.

Preferably, a combination in accordance with the invention comprises zinc or a salt thereof as active agent, preferably zinc gluconate.

It may be, for example, the product sold under the name Gluconal Zn-P by the company Arnaud.

Preferably, a combination in accordance with the invention comprises vitamin B8 and/or vitamin C, preferentially vitamin B8 and vitamin C.

According to a preferred embodiment, a combination in accordance with the invention comprises, besides taurine, a derivative thereof and/or an acceptable salt thereof and a grape extract as defined previously, zinc or a salt thereof, and vitamins.

A combination of the invention may contain, besides the additional active agents indicated previously, one or more divalent mineral cations in various forms.

A divalent mineral cation may thus be in the form of an anhydrous or hydrated mineral or organic salt or a chelated complex. These salts may be, for example, carbonates, bicarbonates, sulfates, glycerophosphates, chlorides, nitrates, acetates, hydroxides, oxides, α-hydroxy acid salts (citrates, tartrates, lactates, malates) or fruit acid salts, or alternatively amino acid salts (aspartate, arginate, fumarate) or fatty acid salts (palmitate, oleate, caseinate, behenate).

A divalent mineral cation may be chosen from manganese, copper and/or zinc or from alkaline-earth metals. As alkaline-earth metals that may be used in the invention, mention may be made of barium, calcium, magnesium, strontium and/or beryllium.

Advantageously, a divalent mineral cation, and especially an alkaline-earth metal, is used in the present invention in salt form. In particular, the salt may be chosen from nitrate, citrate, chloride, gluconate, sulfate, lactate and/or acetate salts.

A divalent mineral cation may also be used in the form of a chelated complex, especially chelated to crystalline or ionized proteins.

A divalent mineral cation may also be in a specific form stored by a microorganism, for example such as a yeast, like selenium yeasts.

According to another embodiment, a composition of the invention may contain non-photosynthetic, non-fructifying filamentous bacteria or bacterial extracts derived from non-photosynthetic, non-fructifying filamentous bacteria as defined according to the classification in Bergey's Manual of Systemic Bacteriology, volume 3, section 23, 9th edition, 1989.

Mention may be made in particular of bacteria belonging to the order of Beggiatoales, and especially bacteria belonging to the genus *Beggiatoa*. Mention may moreover be made of bacteria belonging to the genus *Vitreoscilla*, which is similar to the genus *Beggiatoa*. Among the bacteria that may be used, mention may be made, for example, of *Vitreoscilla beggiatoides* (ATCC 43181) and *Beggiatoa alba* (ATCC33555), and preferentially the use of the extract of *Vitreoscilla filiformis*, in particular with the strain ATCC 15551, metabolites thereof and fractions thereof may be used.

As indicated previously, a combination of active agents in accordance with the invention may comprise, besides taurine, a derivative thereof and/or an acceptable salt thereof and at least one grape extract, at least one arterial pressure modulator.

Arterial pressure biological modulators are known to those skilled in the art.

An arterial pressure modulator in accordance with the invention may be chosen from vitamin D, cysteine, arginine, citrulline, glutamate, tryptophan, leucine, a tripeptide chosen from Val-Pro-Pro (VPP) and isoleucine-proline-proline (IPP), adenosine, flavonoids from berries, onions, pomegranate, red wine, tea, cocoa and dark chocolate, coenzyme Q10 (CoQ), acetyl-L-carnitine, α-lipoic acid, soybean proteins, spirulina; a microorganism such as *Lactobacillus helveticus*, *Bifidobacterium longum*, *Lactobacillus acidophilus*, *L. casei*, *L. acidophilus*, *Saccharomyces cerevisiae*, *Streptococcus thermophilus*; prebiotic agents, chosen especially from oligosaccharides produced from glucose, galactose, xylose, maltose, sucrose, lactose, starch, xylan, hemicellulose and inulin; glutathione, soybean isoflavones (genistin, genistein, daidzin, daidzein, glycitin, glycitein, estradiol, estrone), soybean lecithin and Fruitflow™, or mixtures thereof.

More particularly, the oligosaccharide comprises at least one fructo-oligosaccharide.

More particularly, a prebiotic that is suitable for use in the invention may comprise a mixture of fructo-oligosaccharide and of inulin.

Such an arterial pressure modulator may be present in a combination of active agents in accordance with the invention in a content of between 0.1% and 50% by weight, preferably between 1% and 40% by weight and preferentially between 2% and 30% by weight relative to the total weight of the combination.

According to a particular embodiment, a composition of the invention may also comprise at least one probiotic microorganism, a prebiotic agent or a mixture of probiotic microorganisms and a mixture of prebiotic agents.

Specific examples of probiotic microorganisms that are suitable for use in the invention are *Bifidobacterium adolescentis*, *Bifidobacterium animalis*, *Bifidobacterium bifidum*, *Bifidobacterium breve*, *Bifidobacterium lactis*, *Bifidobacterium longum*, *Bifidobacterium infantis*, *Bifidobacterium pseudocatenulatum*, *Lactobacillus acidophilus* (LC1, NCFB 1748); *Lactobacillus amylovorus*, *Lactobacillus casei* (Shirota), *Lactobacillus rhamnosus* (strain GG), *Lactobacillus brevis*, *Lactobacillus crispatus*, *Lactobacillus delbruckii* (subsp. *bulgaricus*, *lactis*), *Lactobacillus fermentum*, *Lactobacillus helveticus*, *Lactobacillus gallinarum*, *Lactobacillus gasseri*, *Lactobacillus johnsonii*, *Lactobacillus paracasei*, *Lactobacillus plantarum*, *Lactobacillus reuteri*, *Lactobacillus rhamnosus*, *Lactobacillus salivarius*, *Lactobacillus alimentarius*, *Lactobacillus curvatus*, *Lactobacillus casei* subsp. *casei*, *Lactobacillus sake*, *Lactococcus lactis*, *Enterococcus faecalis* or *faecium*, *Lactococcus lactis* subsp. *lactis* or *cremoris*, *Leuconostoc mesenteroides* subsp. *dextranicum*, *Pediococcus acidilactici*, *Sporolactobacillus inulinus*, *Streptococcus salvarius* subsp. *thermophilus*, *Streptococcus thermophilus*, *Staphylococcus carnosus*, *Staphylococcus xylosus*, *Saccharomyces* (*cerevisiae* or *boulardii*), *Bacillus* (*cereus* var. *toyo* or *subtilis*), *Bacillus coagulans*, *Bacillus licheniformis*, *Escherichia coli* strain *nissle*, *Propionibacterium freudenreichii*, and mixtures thereof.

The microorganisms may be formulated in the form of powders, i.e. in a dry form, or in the form of suspensions or solutions.

More particularly, they may be probiotic microorganisms chosen from microorganisms of the genus *Lactobacillus* sp. and/or *Bifidobacterium* sp., a fraction thereof and/or a metabolite thereof. As illustrations of these microorganisms, mention may be made more particularly of *Lactobacillus johnsonii*, *Lactobacillus reuteri*, *Lactobacillus rhamnosus*, *Lactobacillus paracasei*, *Lactobacillus casei*, *Bifidobacterium bifidum*, *Bifidobacterium breve*, *Bifidobacterium longum*, *Bifidobacterium animalis*, *Bifidobacterium lactis*, *Bifidobacterium infantis*, *Bifidobacterium adolescentis* and *Bifidobacterium pseudocatenulatum*, and mixtures thereof.

The species that are most particularly suitable are *Lactobacillus johnsonii*, *Lactobacillus paracasei*, *Bifidobacterium adolescentis*, *Bifidobacterium longum* and *Bifidobacterium lactis* NCC 2818 (also known as Bb12 ATCC 27536), which were deposited, respectively, according to the Treaty of Budapest, at the Institut Pasteur (28, rue du Docteur Roux, F-75024 Paris cedex 15) on 30/06/92, 12/01/99, 15/04/99, 15/04/99 and 07/06/05 under the following designations CNCM I-1225, CNCM I-2116, CNCM I-2168 and CNCM I-2170 and CNCM I-3446, and the genus *Bifidobacterium longum* (BB536). The strain of *Bifidobacterium lactis* CNCM I-3446 may be obtained from Hansen (Chr. Hansen A/S, 10-12 Boege Alle, P.O. Box 407, DK-2970 Hoersholm, Denmark).

According to one particular embodiment of the invention, the composition comprises at least two different microorganisms, which are especially probiotic, and/or metabolites and/or fractions thereof. These microorganisms may differ by their nature, for example bacterium and fungus, or alternatively by their family, their genus or their species, or only by their strain.

The prebiotic agents that are suitable for the invention may be chosen from oligosaccharides, produced from glucose, galactose, xylose, maltose, sucrose, lactose, starch, xylan, hemicellulose, inulin, gums of acacia type, for example, or a mixture thereof. More particularly, the oligosaccharide comprises at least one fructo-oligosaccharide.

More particularly, this prebiotic may comprise a mixture of fructo-oligosaccharide and of inulin.

According to one embodiment, a combination of the invention may comprise additional hydrophilic active agents. Hydrophilic active agents that may be used include proteins or protein hydrolysates, amino acids, polyols, especially of $C_2$ to $C_{10}$, for instance glycerol, sorbitol, butylene glycol or polyethylene glycol, urea, allantoin, sugars and sugar derivatives, water-soluble vitamins, starch, and bacterial or plant extracts, for instance those from Aloe vera.

According to another embodiment, a combination of the invention may also comprise a lipophilic active agent. Lipophilic active agents that may be used include retinol (vitamin A) and derivatives thereof, ceramides and essential oils.

According to a preferred embodiment, a combination in accordance with the invention comprises, besides taurine or a derivative thereof and a grape seed extract as defined previously, zinc gluconate, vitamin B8 and optionally vitamin C.

Composition and Kits

According to one aspect of the invention, a combination of active agents in accordance with the invention may be used in a cosmetic composition that is suitable for oral administration.

A composition in accordance with the invention comprises a physiologically or pharmaceutically acceptable medium.

Needless to say, a person skilled in the art will take care to select the additional active agents and the amount thereof such that the advantageous properties of the composition in accordance with the invention are not, or are not substantially, adversely affected by the envisaged addition.

A cosmetic composition in accordance with the invention may comprise taurine, a derivative thereof and/or an acceptable salt thereof in a content of between 1% and 30% by weight relative to the total weight of the composition, expressed as taurine equivalent.

Preferably, taurine, a derivative thereof and/or an acceptable salt thereof is present in a content of between 5% and 20% by weight and preferentially between 10% and 15% by weight relative to the total weight of the composition, expressed as taurine equivalent.

In addition, a cosmetic composition in accordance with the invention comprises a grape extract, in particular a grape seed extract, as defined previously, in a content of between 1% and 80% by weight relative to the total weight of the composition.

Preferably, the grape extract is present in a content of between 5% and 70% by weight and preferably between 10% and 60% by weight relative to the total weight of the composition.

A composition in accordance with the invention may also comprise the additional cosmetic active agents indicated previously. They may be present in a composition in accordance with the invention in an amount of between 0.0001% and 20% by weight relative to the total weight of the composition.

More particularly, zinc or a salt thereof may be used in a composition in accordance with the invention in an amount of between 0.1% and 30% by weight relative to the total weight of the composition. Preferably, zinc or a salt thereof may be used in a content of between 0.5% and 20% by weight and preferentially between 1% and 10% by weight relative to the total weight of the composition.

Vitamin B8 in accordance with the invention may be used in a composition in accordance with the invention in a content of between 0.0001% and 1% by weight relative to the total weight of the composition. Preferably, vitamin B8 may be used in a content of between 0.0005% and 0.5% by weight and preferentially between 0.001% and 0.1% by weight relative to the total weight of the composition.

Furthermore, vitamin C in accordance with the invention may be used in a composition in accordance with the invention in a content of between 0.5% and 25% by weight relative to the total weight of the composition. Preferably, vitamin C may be used in a content of between 1% and 20% by weight and preferentially between 2% and 10% by weight relative to the total weight of the composition.

A combination of active agents and a composition in accordance with the invention make it possible, via their oral administration, to improve, reinforce or restore an aesthetic state of a nail.

As indicated previously, various intrinsic or extrinsic factors may be the cause of an aesthetically degraded state of the nails. The object of the present invention is to restore this state without treating it or preventing its cause, and is thus limited to the cosmetic field. The invention does not relate to the therapeutic field.

According to one embodiment, the invention is directed towards reducing and/or preventing an impairment in the structure of the nails, in particular to reduce and/or prevent brittle, fragile, soft, split or cracked nails, preferably split nails.

For the purposes of the invention, the expression "impairment in the structure of the nails" means an impairment in the organization of the keratin fibres or in their chemical composition constituting the nails with regard to an organization or a composition observed in nails of good aesthetic quality.

More particularly, the impairments in the structure of the nails may lead to the presence of striations on the surface of the nails. Thus, the invention is also directed towards reducing and/or preventing striated nails.

According to one embodiment, the combination of active agents under consideration in the invention promotes and/or improves the flexibility and/or hardness of the nails. Following the use of the combination in accordance with the invention, the nails are found to be less brittle, harder, more flexible, and/or more resistant to impacts, and have less of a tendency to split.

According to one embodiment, the combination of active agents in accordance with the invention also makes it possible to make the nails sleek, shiny and/or translucent.

In particular, the combination of active agents in accordance with the invention makes it possible to increase the transparency and/or whiteness and/or sheen of the nails, as indicated in the tests presented hereinbelow.

According to one embodiment, the combination of active agents in accordance with the invention also makes it possible to improve the general aesthetic appearance of the nails.

According to the present invention, it is considered that the general aesthetic appearance of a nail is improved when at least one of the parameters chosen from the hardness, the solidity, the resistance to impacts or to external attacking factors, the resistance to splitting, the sleek appearance and/or the sheen is improved. This improvement in the general aesthetic appearance is illustrated in the table of Example 2.3.

The combination of active agents in accordance with the invention or the composition in accordance with the invention is administered orally.

The combinations and compositions in accordance with the invention, intended for oral administration, may especially comprise all or only part of the daily dose.

The required daily dose may thus be divided up so as to be taken, for example, 1 to 3 times in the day.

Typically, the duration of this cosmetic treatment may be longer than 4 weeks, especially from 4 to 15 weeks, with, where appropriate, one or more periods of stoppage.

The oral route has the advantage of acting in a more overall manner on the whole of the structure of the nails.

The expression "oral cosmetic composition" means, for example, nutritional, nutraceutical or cosmeceutical compositions, comprising at least a combination according to the invention.

In the case of compositions that are suitable for oral administration, the use of an ingestible support is preferred. The ingestible support may be of diverse nature according to the type of composition under consideration.

For ingestion, numerous embodiments of oral compositions and especially of food supplements are possible.

Such compositions may be formulated via any common process known to those skilled in the art.

Thus, a composition in accordance with the invention may preferably take the form of a coated tablet, a gel capsule, a suspension, a gel, an emulsion, a drinkable solution, a tablet to be swallowed or chewed, a capsule, especially a soft or hard capsule, a granule to be dissolved, a syrup, a lozenge or a food supplement.

In particular, a combination of active agents in accordance with the invention may be incorporated into any form of food supplement or enriched food, for example food bars or compacted or loose powders. The powders may be diluted with water, in soda, dairy products or soybean derivatives, or may be incorporated into food bars.

According to one preferred embodiment, a composition in accordance with the invention administered orally may be formulated in the form of coated tablets, gel capsules, gels, emulsions, tablets, capsules, hydrogels, food bars, compact or loose powders, liquid suspensions or solutions, confectionery products, fermented milks, fermented cheeses, chewing gums, toothpastes or spray solutions.

Milk, yoghurt, cheese, fermented milks, milk-based fermented products, ice creams, fermented or non-fermented cereal-based products, milk-based powders, infant and baby formulas, animal feed in particular for pets, tablets or lozenges, liquid bacterial suspensions, oral supplements in dry form and oral supplements in liquid form are, for example, suitable as food supports.

The oral compositions may be either in anhydrous form or in aqueous form.

A combination of active agents in accordance with the invention may be formulated with the usual excipients and components for such oral compositions or food supplements, i.e. especially fatty and/or aqueous components, humectants, thickeners, preserving agents, texture agents, taste agents and/or coating agents, antioxidants, preserving agents and dyes that are common in the food sector.

The formulating agents and excipients for oral compositions, and especially for food supplements, are known in this field and are not the subject of a detailed description herein.

In particular, a composition in accordance with the invention may be a food composition for human consumption. This may be, in particular, nutritional complete foods, drinks, mineral waters, soups, dietary supplements and replacement or substitute foods, nutritional bars, confectionery, milk-based products or fermented milk-based products, yoghurts, milk-based powders, enteral nutritional products, infant and/or baby compositions, fermented or non-fermented cereal-based products, ice creams, chocolate, coffee, "culinary" products such as mayonnaise, tomato puree or salad dressings.

According to one embodiment, a kit according to the invention uses an antifungal agent. Such an agent may be chosen from the families of imidazoles, morpholines or pyridones.

According to another embodiment, a kit according to the invention uses a moisturizer and/or a hardener.

A moisturizer in accordance with the invention may be chosen from vitamins and oils. As examples of oils that are suitable for use as moisturizers, mention may be made especially of argan oil, sesame seed oil and sunflower oil.

A hardener in accordance with the invention may be chosen from hydrolysed wheat proteins, calcium pantothenate or vitamin B5, iron, epoxy resins and polyesters, and nitrocellulose.

Process

According to another of its aspects, the present invention relates to a cosmetic process for reducing and/or preventing brittle, fragile, soft, split or cracked nails, preferably split nails, in an individual in need thereof, characterized in that it comprises at least the oral administration, to the said individual, of a combination or of a composition in accordance with the invention.

A process according to the invention may comprise a step that consists in observing a reduction in, or even disappearance of, the impairment in the quality of the nails.

Advantageously, the application of a process of the invention gives the advantages indicated previously as being associated with the use of a combination or of a composition in accordance with the invention, and may especially improve, or even restore, the hardness, the resistance to impacts, a physiological form, a sleek appearance or a translucent appearance.

A cosmetic process according to the invention may be performed especially by administering a food composition as defined above.

A process of the invention may be performed on a daily basis, for example, for instance at a rate of one single administration per day or one administration twice a day, for example once in the morning and once in the evening, or three times a day, in particular at each meal.

A cosmetic process according to the invention may be performed, for example, by daily administration of a composition formulated, for example, in the form of gel capsules, coated tablets, emulsions, tablets, capsules or drinkable vials, in appropriate amount and number, depending on their form.

An effective amount of a combination in accordance with the invention may be administered in a single dose per day or in divided doses over the day, for example two to three times a day.

A process according to the invention may advantageously comprise a single administration.

A cosmetic process may be performed over a time period ranging from one week to several weeks, or even several months, this period moreover possibly being repeated after periods without treatment, for several months or even several years.

By way of example, the administration of a combination of active agents in accordance with the invention may be performed at a rate, for example, of three times a day, generally over a prolonged period of at least 4 weeks, or even 4 to 15 weeks, optionally comprising one or more periods of stoppage or being repeated after a period of stoppage.

In the description and the examples that follow, unless otherwise mentioned, the percentages are weight percentages and the ranges of values written in the form "between . . . and . . . " include the stated lower and upper limits. The ingredients are mixed, before being formed, in the order and under conditions that are easily determined by those skilled in the art.

The examples hereinafter are presented as nonlimiting illustrations of the field of the invention.

EXAMPLES

Example 1

Oral Composition in Tablet Form

| Ingredients | (mg/tablet) | (% by weight relative to the total weight of the composition) |
|---|---|---|
| Taurine[1] | 75 | 10.641 |
| Zinc gluconate[2] | 25.74 | 3.652 |
| Grape seed extract[3] | 93.5 | 13.266 |
| Vitamin B8[4] | 0.016 | 0.002 |
| Vitamin C[5] | 18.34 | 2.602 |
| Excipients for the core | | |
| Dibasic calcium phosphate dihydrate | 218 | 30.931 |
| Microcrystalline cellulose | 214 | 30.363 |
| Croscarmellose sodium | 20 | 2.838 |
| Silicon dioxide | 7 | 0.993 |
| Magnesium stearate | 6 | 0.851 |
| Film-coating agents | | |
| Hydroxypropylmethyl-cellulose | 9.18 | 1.303 |
| Hydroxypropylcellulose | 9.18 | 1.303 |
| Talc | 5.44 | 0.772 |
| Titanium dioxide | 3.21 | 0.455 |
| Yellow iron oxide | 0.12 | 0.017 |
| Red iron oxide | 0.07 | 0.010 |

[1]sold under the name Taurine by the company Quimdis
[2]sold under the name Gluconal Zn—P by the company Arnaud
[3]sold under the name Vitaflavan 50 by the company DRT
[4]sold under the name D-Biotin by the company DSM
[5]sold under the name Ascorbic acid 90% granulation by the company DSM One to three of these tablets may be taken per day.

This composition may be prepared according to the process described below:

The D-biotin and the excipients are first mixed together. Next, the taurine, the zinc gluconate, the grape seed extract and the vitamin C are added to this mixture.

The mixture thus obtained is then lubricated and compressed, before being coated with the film-coating agents and purified water.

Example 2

A single-blind study was performed, on the basis of the composition of Example 1, under dermatological control, on 50 healthy women from 18 to 50 years old, having brittle/split nails.

These women were supplemented for 3 months with the composition of Example 1, at a rate of two tablets per day.

The efficacy of the supplementation was then validated by clinical scoring and self-evaluation.

The results obtained are presented in the tables below.

1. Onychoschizia Clinical Scores

TABLE 1

| | Mean | | | |
|---|---|---|---|---|
| | T0 | T1 month | T2 months | T3 months |
| Lamellar separation (1) | 1.47 | 1.06 | 0.76 | 0.71 |
| Longitudinal separation (2) | 0.20 | 0.08 | 0.00 | 0.02 |
| Onychoschizia score (1 + 2) | 1.67 | 1.14 | 0.76 | 0.73 |

The onychoschizia score decreases in a significant manner from 1 month of supplementation with the combination according to the invention, demonstrating the efficacy of the formulation on splitting of the nails.

2. Overall Clinical Efficacy Score

The overall clinical score measures the change between times T0 and T1 month, T0 and T2 months and T0 and T3 months in the embrittled nature of the nail.

This score is evaluated by means of a 5-point scale as indicated in the table below. The results are presented in terms of number and frequency.

TABLE 2

| | T1 month | T2 months | T3 months |
|---|---|---|---|
| 0 Deterioration | 4% | 2% | 0% |
| 1 No improvement | 38% | 21% | 30% |
| 2 Moderate | 27% | 42% | 39% |
| 3 Good | 31% | 35% | 29% |
| 4 Excellent | 0% | 0% | 2% |

From 1 month of supplementation with the combination in accordance with the invention, the clinician notes a marked improvement in the embrittled nature of the nail for 58% of the individuals.

The improvement concerns 77% and 70% of the women after, respectively, 2 and 3 months of supplementation.

3. Self-Evaluation of the Quality of the Nails by the Individuals of the Study

TABLE 3

| Population | | T1 month % | T2 months % | T3 months % |
|---|---|---|---|---|
| With the supplementation, my nails split less | Entirely in agreement | 4.1 | 24.5 | 24.5 |
| | Quite in agreement | 40.8 | 38.8 | 53 |
| | Remotely in agreement | 36.7 | 24.5 | 14.3 |
| | Not at all in agreement | 18.4 | 12.2 | 8.2 |
| | No opinion | 0 | 0 | 0 |
| With the supplementation, my nails crack less | Entirely in agreement | 2.0 | 8.2 | 16.3 |
| | Quite in agreement | 44.9 | 46.9 | 53.1 |
| | Remotely in agreement | 38.8 | 34.7 | 30.6 |
| | Not at all in agreement | 0 | 6.1 | 14.3 |
| | No opinion | 0 | 4.1 | 0 |
| With the supplementation, my nails appear to be less damaged | Entirely in agreement | 6.1 | 18.4 | 26.5 |
| | Quite in agreement | 42.9 | 42.9 | 49.0 |
| | Remotely in agreement | 32.7 | 26.5 | 20.4 |
| | Not at all in agreement | 18.4 | 8.2 | 4.1 |
| | No opinion | 0 | 4.1 | 0 |

TABLE 3-continued

| Population | | T1 month % | T2 months % | T3 months % |
|---|---|---|---|---|
| With the supplementation, my nails are less brittle | Entirely in agreement | 4.1 | 10.2 | 10.2 |
| | Quite in agreement | 40.8 | 44.9 | 55.1 |
| | Remotely in agreement | 28.6 | 38.8 | 30.6 |
| | Not at all in agreement | 16.3 | 16.3 | 4.1 |
| | No opinion | 0 | 0 | 0 |
| With the supplementation, my nails are less striated | Entirely in agreement | 4.1 | 12.2 | 14.3 |
| | Quite in agreement | 32.7 | 38.8 | 49.0 |
| | Remotely in agreement | 40.8 | 30.6 | 28.6 |
| | Not at all in agreement | 16.3 | 12.2 | 6.1 |
| | No opinion | 6.1 | 6.1 | 2.0 |
| With the supplementation, my nails are more solid | Entirely in agreement | 10.2 | 20.4 | 22.4 |
| | Quite in agreement | 32.7 | 34.7 | 44.9 |
| | Remotely in agreement | 34.7 | 32.7 | 28.6 |
| | Not at all in agreement | 20.4 | 10.2 | 4.1 |
| | No opinion | 2.0 | 2.0 | 0 |
| The food supplement makes my nails shinier | Entirely in agreement | 4.1 | 8.2 | 16.3 |
| | Quite in agreement | 20.4 | 34.7 | 51.0 |
| | Remotely in agreement | 32.7 | 34.7 | 30.6 |
| | Not at all in agreement | 22.4 | 14.3 | 2.0 |
| | No opinion | 20.4 | 8.2 | 0 |
| The food supplement makes my nails more beautiful | Entirely in agreement | 2.0 | 14.3 | 22.4 |
| | Quite in agreement | 26.5 | 32.7 | 40.8 |
| | Remotely in agreement | 34.7 | 38.8 | 32.7 |
| | Not at all in agreement | 18.4 | 14.3 | 2.0 |
| | No opinion | 18.4 | 0 | 2.0 |

The majority of the women participating in the study noted the efficacy of the combination in accordance with the invention.

The invention claimed is:

1. Oral cosmetic method of improving the quality of the nails in a person in need thereof comprising at least the step of orally administering to said person a combination of active agents comprising at least taurine, a derivative thereof and/or an acceptable salt thereof and at least one grape extract, as cosmetic active agents.

2. Method according to claim 1, in which the grape extract is a grape seed extract.

3. Method according to claim 1, for reducing brittle, fragile, soft, split or cracked nails.

4. Method according to claim 1, for reducing striated nails.

5. Method according to claim 1, for making the nails sleek, shiny and/or translucent.

6. Method according to claim 5, for increasing the transparency and/or whiteness and/or sheen of the nails.

7. Method according to claim 1, for improving the general aesthetic appearance of the nails.

8. Method according to claim 1, wherein the combination also comprises, as additional active agent, zinc or a salt thereof.

9. Method according to claim 1, wherein the combination also comprises, as additional active agents, vitamins.

10. Method according to claim 9, wherein the combination also comprises, as additional active agents, vitamin B8 and/or vitamin C.

11. Method according to claim 1, in which the combination of active agents is used in a cosmetic composition that is suitable for oral administration, the said composition being in the form of a coated tablet, a gel capsule, a suspension, a gel, an emulsion, a drinkable solution, a tablet to be swallowed or chewed, a capsule, a granule to be dissolved, a syrup, a lozenge or a food supplement.

12. Method according to claim 11, in which taurine, a derivative thereof and/or an acceptable salt thereof is used in a content of between 1% and 30% by weight relative to the total weight of the composition, expressed as taurine equivalent.

13. Method according to claim 12, in which taurine, a derivative thereof and/or an acceptable salt thereof is used in a content of between 10% and 15% by weight relative to the total weight of the composition, expressed as taurine equivalent.

14. Method according to claim 11, in which the grape extract is used in a content of between 1% and 80% by weight, relative to the total weight of the composition, expressed as polyphenol dose.

15. Method according to claim 14, in which the grape extract is used in a content of between 10% and 60% by weight, relative to the total weight of the composition, expressed as polyphenol dose.

16. Method according to claim 11, in which zinc is used in a content of between 0.1% and 30% by weight, relative to the total weight of the composition.

17. Method according to claim 16, in which zinc is used in a content of between 1% and 10% by weight, relative to the total weight of the composition.

* * * * *